United States Patent [19]

Wang

[11] Patent Number: 4,799,494

[45] Date of Patent: Jan. 24, 1989

[54] PERCUTANEOUS ASPIRATION LUNG BIOPSY NEEDLE ASSEMBLY

[76] Inventor: Ko P. Wang, 11006 Nacirema La., Stevenson, Md. 21153

[21] Appl. No.: 921,471

[22] Filed: Oct. 22, 1986

[51] Int. Cl.⁴ ............................................. A61B 10/00
[52] U.S. Cl. ...................................... 128/753; 604/51
[58] Field of Search ............... 128/672, 673, 749–754, 128/763, 770; 604/51.158, 159, 163, 164

[56] References Cited

U.S. PATENT DOCUMENTS

| | | | |
|---|---|---|---|
| Re. 30,966 | 6/1982 | Hargers et al. | 128/673 |
| 2,516,492 | 7/1950 | Turkel | 128/751 |
| 3,175,554 | 3/1965 | Stewart | 128/754 |
| 3,183,722 | 5/1965 | Unger et al. | 128/673 |
| 3,500,828 | 3/1970 | Podhora . | |
| 3,598,108 | 8/1971 | Jamshidi . | |
| 3,628,524 | 12/1971 | Jamshidi . | |
| 3,630,192 | 12/1971 | Jamshidi . | |
| 4,052,989 | 10/1977 | Kline . | |
| 4,295,441 | 3/1981 | Pratt . | |
| 4,508,103 | 4/1985 | Calisi | 128/673 |
| 4,517,844 | 5/1985 | Powell | 128/672 |
| 4,532,935 | 8/1985 | Wang . | |
| 4,600,014 | 7/1986 | Beraha | 128/754 |
| 4,617,940 | 10/1986 | Wang | 128/753 |
| 4,619,272 | 10/1986 | Zambelli | 128/753 |

FOREIGN PATENT DOCUMENTS 3018864 11/1981 Fed. Rep. of Germany ...... 128/672
3044626 6/1982 Fed. Rep. of Germany ...... 604/164

OTHER PUBLICATIONS

Kormed, Inc., Brochure: "The Jamshidi Soft-Tissue Biopsy Needle/Syringe", Not Dated.

Primary Examiner—Max Hindenburg
Attorney, Agent, or Firm—Cushman, Darby & Cushman

[57] ABSTRACT

Percutaneous aspiration lung biopsy needle assembly comprises a hollow outer needle in which a second hollow needle of smaller diameter is disposed, the second inner needle being retractable from a first extended position to a second retracted position within the first needle. The inner needle, which extends for only a portion of the distance has a bevelled tip and is constructed such that its outer diameter closely matches the inner diameter of the outer needle. When the inner needle is in its extended position the needle assembly may be forced through the skin and into the lung with relative ease. Subsequently, the inner needle is retracted so that only the flat-tipped duller edged outer needle is exposed, thereby allowing a large tissue sample, suitable for histological examination, to be obtained. A pressure monitor is engaged with the needle apparatus to more accurately determine when lung and tumor entries are achieved. The assembly minimizes the risk of pneumothorax, excessive bleeding and embolism, and additionally allows continuous fluoroscopy of the target site without exposure of the physician's hand to x-rays.

9 Claims, 2 Drawing Sheets

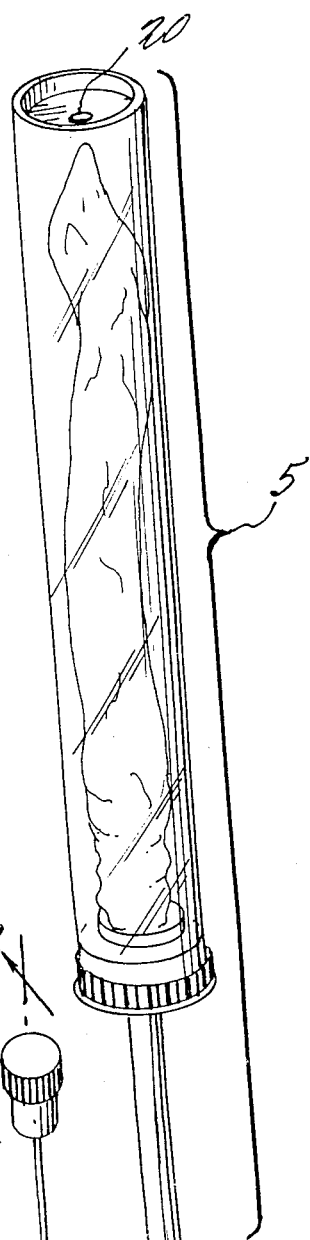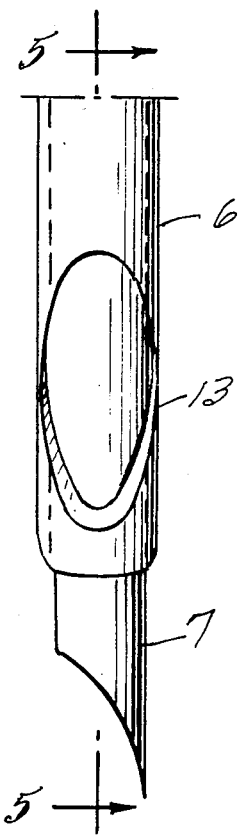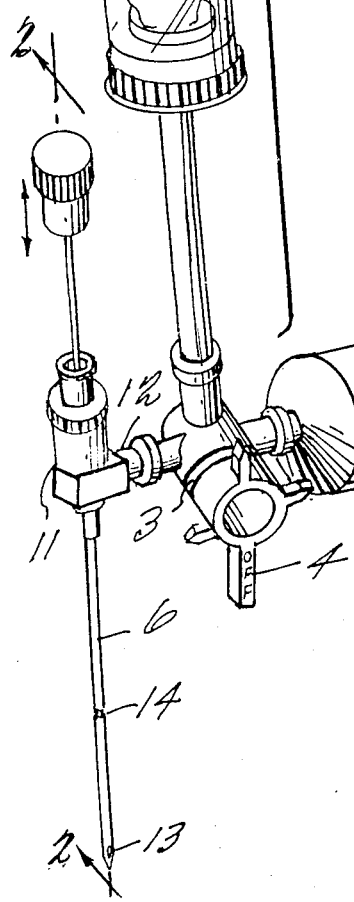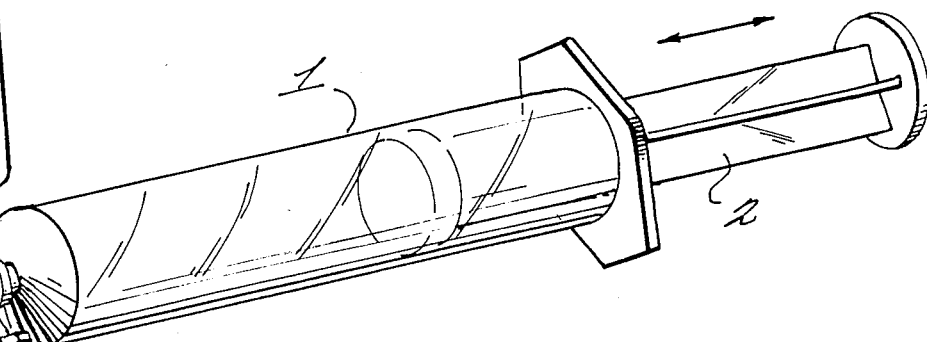
FIG. 4
FIG. 5
FIG. 1

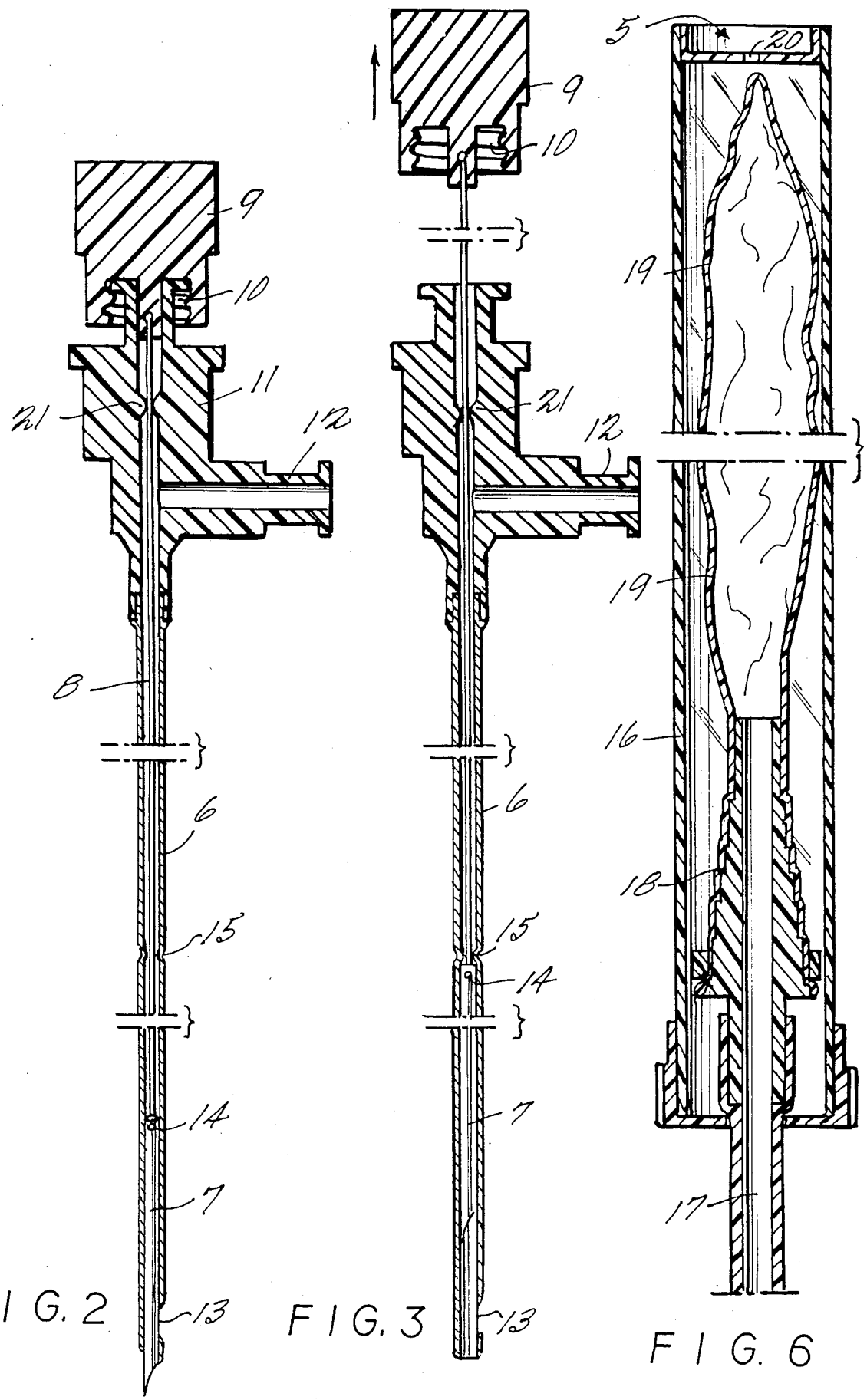

PERCUTANEOUS ASPIRATION LUNG BIOPSY NEEDLE ASSEMBLY

BACKGROUND OF THE INVENTION

The present invention relates to a percutaneous aspiration lung biopsy needle assembly for safe extraction of biopsy tissue and/or fluids from the lungs. Percutaneous needle lung biopsy or transthoracic needle lung biopsy involves the use of a needle to enter the lung through the skin to obtain a biopsy sample. Such a procedure has many risks. These risks may be so great that invasive surgical procedures such as open lung biopsy may be preferred in certain instances. This is so, for example, if the lung biopsy needle is punched into a blood vessel, since uncontrollable bleeding may occur. The degree of bleeding largely depends on the size and shape of the lung biopsy needle which is used. In general, the larger the diameter of the needle, the greater the chance of uncontrollable bleeding. With regard to the shape of the needle tip, a bevelled shape is known to produce fewer bleeding problems than a flat tipped or a standard tapered needle tip.

A second risk of percutaneous lung biopsy is pneumothorax, i.e., lung collapse. When percutaneous biopsy is performed, since the lung itself is punctured, air may leak from the lung and accumulate between the lung surface and the chest cage. If this condition becomes severe the patient may require a chest tube to drain the air from the chest cavity, and the condition may sometimes be fatal.

Pneumothorax results from a number of factors. Theoretically, if the lung is punctured by a needle it might be expected that leakage from the lung would occur. Experimental evidence shows, however, that even larger holes in the lung (for example holes produced by biopsy with forceps) seal off quite rapidly as a result of blood or other secretion near the hole. Experience further shows that the use of larger needles for lung biopsy results in about a 25 percent occurrence of pneumothorax. This apparently conflicting data indicates that pneumothorax may not be caused by the larger hole created by the larger needle, rather it is because when a larger needle is used, the rigidity of the needle against the lung tissue may result in tearing or stretching of the tissue at the point of entry, such that leakage may occur while the needle is in place.

While bleeding and pneumothorax are risks involved where a larger relatively stiff needle and/or flat-tipped needles are used, the use of a smaller diameter needle, such as a 22 gauge needle having a bevelled tip, is also undesirable because the sample obtained using such a smaller needle may be insufficient for histological examination rather than cytological examination. Histological examination is preferred, however, since certain diseases may not be diagnosed cytologically. Historically, the sample size required for histological examination has required open lung biopsy.

At best, then, needles currently used for percutaneous lung biopsy must strike a balance between flexibility and stiffness (as determined by needle diameter) to minimize the chance of lung collapse and improve the sample size, and also balance between the use of sharp bevelled needle tips and dull tips in order to maximize the ability to pierce the skin and other tissue, but minimize chance of uncontrollable bleeding.

A third danger of percutaneous lung biopsy is air embolism. This happens when the needle enters a vessel in the lung and when the stylet is removed to apply negative suction. Air sucked into the vessel in this manner may markedly decrease the pressure in the vessel. When air gets into the vessel it travels to vital organs and blocks the blood supply and the patient can expire.

A further problem encountered during lung biopsy procedures arises in the manipulation of the needle assembly itself. In order to locate the target tissue x-ray fluoroscopy is generally used. Thus, to avoid exposure of the physician's hand to x-radiation during the procedure, the needle will generally be inserted to the approximate location desired with the fluoroscope system off. The physician's hand is then removed from the needle which is, of course, positioned between the x-ray source and the sampling site. The fluoroscope system is then turned on so that the physician may determine the position of the needle relative to the sampling site. The physician then again removes his or her hand and the needle position is determined again. This procedure is repeated until the desired sample is obtained.

Thus, it would be desirable to obtain lung biopsy samples in a manner which would allow continuous fluoroscopy without exposing the physician's hand to x-radiation, and thus speed the procedure.

SUMMARY OF THE INVENTION

The present invention, therefore, is a percutaneous aspiration lung biopsy needle assembly which minimizes bleeding and pneumothorax risks during the procedure, yet achieves sampling of specimens large enough for histological examination while at the same time allowing continuous fluoroscopy without unnecessary exposure of the physician's hand to x-rays.

In a preferred embodiment, the assembly comprises a hollow outer needle within which a second hollow needle of smaller diameter is disposed, the second inner needle being retractable from a first extended position to a second retracted position within the first needle. The inner needle has a bevelled tip and is constructed such that its outer diameter closely matches the inner diameter of the outer needle. When the inner needle is in its extended position the needle assembly may be forced through the skin and into the lung with relative ease. Subsequently, the inner needle may be retracted so that only the flat-tipped duller edged outer needle is exposed, thereby minimizing the chance of uncontrollable bleeding. The inner needle is hollow and extends only a short distance from the tip of the outer needle along the interior shaft of the outer needle, and is at that point connected to small gauge solid stylet. Thus, improved flexibility is achieved such that the chance of pneumothorax is minimized.

The solid stylet extends from the inner hollow needle to the proximal end of the outer needle so that it may be manually retracted in use. At the distal end of the needle assembly, and generally at right angles thereto, a side arm is positioned so that a syringe may be sealably engaged to the needle assembly. The positioning of the syringe at right angles to the needle assembly provides the additional benefit of allowing the syringe to act as a handle. Of course, the syringe may be placed at other angles as long as it allows the use of the syringe as a handle during use. Since the syringe is positioned at an angle to the needle, the physician may now use continuous fluoroscopy over the area of needle entry without exposing his or her hand to x-rays. In this manner, the old technique of having to position the needle, release it to determine its location within the body by fluoroscopy, and subsequently reposition the needle again and again, is made obsolete. Naturally, the ability to insert the needle quicker and more accurately using the present invention also enhances its improved safety characteristics.

Of course, the needle within a needle apparatus is advantageously used even without having the syringe as a handle, however, such a syringe-as-handle embodiment is preferred.

A seal is conveniently provided at the distal end of the needle assembly when the syringe is attached by means of a side-arm so that the solid stylet and therefore the inner needle may be retracted without losing the seal at this point. Thus, withdrawal of the plunger within the syringe once the point of sampling is reached will transmit suction pressure to the tip of the outer needle, the inner needle and solid stylet having been retracted, in order to sample the desired tissue.

In this manner, the use of an inner bevelled needle in an extended position during entry of the assembly into the body minimizes bleeding risks, while when the inner needle is retracted, samples appropriate for histological examination can be obtained by use of a larger diameter, flat-tipped, needle. The danger of pneumothorax is minimized since the stiffness of the needle assembly is minimized by using a hollow inner needle in conjunction with a smaller diameter solid stylet.

In the preferred embodiment a three-way stopcock is disposed between the side arm of the needle assembly and the syringe, and a pressure monitor attached thereto. In use, this pressure monitor is designed to show the increased pressure at the needle tip when lung entry is achieved, and the subsequent decrease in pressure when the needle tip enters the tissue to be sampled. In this manner, greater accuracy may be achieved in sampling and improved safety results since less time is spent locating the desired sampling site.

BRIEF DESCRIPTION OF THE ACCOMPANYING DRAWINGS

Reference will hereinafter be made to the accompanying drawings wherein like reference numerals throughout the specification refer to like structure elements and wherein:

FIG. 1 is a representative perspective view of the preferred embodiment of the lung biopsy needle assembly in accordance with the present invention;

FIG. 2 is a cross-section of a portion of the lung biopsy needle assembly taken along line 2—2 of FIG. 1 showing the inner needle in a fully extended position;

FIG. 3 is a cross-sectional view as in FIG. 2, except that the inner needle is shown in a retracted position;

FIG. 4 is an enlarged scale side view of the inner and outer needles, showing the inner needle in a fully extended position;

FIG. 5 is a cross-sectional view along line 5—5 of FIG. 4; and

FIG. 6 is a cross-sectional view of the pressure monitor of the invention.

DESCRIPTION OF THE DRAWINGS

FIG. 1 is a representative perspective view of the biopsy needle assembly showing syringe barrel 1 having within it syringe plunger 2 which is movable within syringe barrel 1 in the usual manner. Naturally, withdrawal of syringe handle 2 through syringe barrel 1 results in the generation of negative pressure within barrel 1.

Sealably attached to syringe barrel 1 is three-way stop cock 3 which may be used to direct communication of pressure within the assembly to the various portions thereof. Manipulation of stop cock handle 4 is used for this purpose. Sealably engaged to one leg of stop cock 3 is pressure monitor assembly 5, which is described in further detail with regard to FIG. 6 below.

Outer needle 6 of the biopsy assembly is also sealably engaged with stop cock 3 via side-arm 12. Housed within outer needle 6 is solid stylet 8 and hollow inner needle 7 (not shown in FIG. 1). Solid stylet 8 is attached to stylet cap 9 which is shown in a retracted position. It is in this position that tissue sampling would occur within the lung, stylet cap 9 and stylet 8 having been retracted after insertion of outer needle 6 through the patient's skin to the desired location for sampling.

A housing portion 11 of the needle assembly may be threadably engaged with stylet cap 9 as shown in FIGS. 2 and 3. Both FIGS. 2 and 3 are cross-sectional views of needle 6 taken along line 2—2 of FIG. 1, showing housing 11 and stylet cap 9. FIG. 2 shows inner needle 7 in a fully extended position, stylet cap 9 having been twisted down onto threaded portion 10 so as to sealably engage with housing 11.

As can be seen in FIG. 2 the channel within side-arm 12 communicates with the interior of outer needle 6. Solid stylet 8 is attached at one end to stylet cap 9 and at the other to the upper end of inner needle 7. Stylet 8 and inner needle 7 are connected at opening 14. Stylet 8 may simply be hooked through opening 14 or may be otherwise firmly joined to inner needle 7 to eliminate the possibility of inner needle 7 becoming loose at any time. Along the distal portion of outer needle 6 a side opening 13 is used. Side opening 13 allows for the collection of a larger sample suitable for histological examination. As can be seen from FIGS. 2 and 3, however, while inner needle 7 is in its extended position, tissue may not enter the lumen of needle 6. Within housing 11 seal 21 surrounds stylet 8 so that pressure communication is directed from within needle 6 to through side-arm 12 and stop-cock 3 into syringe barrel 1. Seal 21 provides a safety seal which, when stylet 8 is withdrawn while inside the patients body, prevents air from being sucked into a blood vessel, thereby minimizing the hazard of embolism.

Hollow inner needle 7 is shown retracted in FIG. 3. Indented portion 15 of outer needle 6 prevents inner needle 7 from unintentionally being retracted too far. Thus, seal 21 within housing 11 cannot be damaged by pulling inner needle 7 all the way out of outer needle 6.

FIG. 4 is an enlarged scale view of the tip of both inner needle 7 and outer needle 6 wherein inner needle 7 is in a fully extended position. Side hole 13 on outer needle 6 is also shown. It is in this position that the physician would force the needle assembly through the skin of the patient to the desired sampling point, inner needle 7 subsequently being retracted prior to sampling.

A cross-sectional view of needles 6 and 7 taken along line 5—5 of FIG. 4 is shown in FIG. 5. As can be seen, inner needle 7 is hollow and has an outer diameter which closely matches the inner diameter of outer needle 6. By using a hollow, retractable inner needle having a sharp bevelled tip, the present needle assembly achieves sufficient needle flexibility to minimize the occurrence of pneumothorax. Further, since inner needle 7 may be retracted, only the dull flat tipped end of outer needle 6 will be exposed during most of the biopsy procedure thereby minimizing the chances of uncontrollable bleeding. Also, the larger outer diameter of outer needle 6 allows for the sampling of a large enough portion of tissue for histological examination.

FIG. 6 is a detailed cross-sectional view of the pressure monitor used in the preferred embodiment of the present invention. This portion of the biopsy needle assembly is used to indicate changes in pressure at the needle tip during insertion and sampling. The pressure monitor 5 includes pressure communicating tube 17 held within outer housing 16. Also within outer housing 16 is holding member 18. The open end of balloon 19 is forced over holding member 18 such that the interior of balloon 19 communicates with tube 17. Hole 20 at one end of housing 16 allows air surrounding balloon 19 to escape if the balloon expands and to enter if the balloon contracts.

Referring again to FIG. 1 it can be seen that in preparation for insertion of outer needle 6 into the patient's lung, stylet cap 9 would be forced down upon and engaged with housing 11 such that stylet 8 and inner needle 7 would be forced to an extended position within outer needle 6. Handle 4 of stop cock 3 would be positioned such that communication from the needle tip through needle 6, side-arm 12, stop cock 3 and into pressure monitor 5 was achieved. The physician would hold syringe barrel 1, forcing down on the needle assembly through the patient's chest wall. Continuous monitoring of the position of the needle tip relative to the target site is monitored by fluoroscopy. Since the x-ray source for the fluoroscope would be directly above the tip of outer needle 6, the hand of the physician is not exposed.

While needles of various sizes are used for lung biopsy according to the present invention, outer needle 6 will generally be 10-20 centimeters in length. Needle 6 is preferably a 19.5 gauge needle, while inner needle 7 is preferably a 22 gauge needle.

As the tip of outer needle 6 enters the pleural space between the chest wall and the lung balloon 19 registers little or no change in pressure. As the needle tip enters the lung, however, an increase in pressure is registered by an expansion of balloon 19. Referring to a fluoroscopy monitor, the physician may then force the tip of the needle into the tissue site to be sampled and the pressure registered at pressure monitor 5 will show a decrease in pressure by slight deflation of balloon 19.

At this point in the procedure the fluoroscope monitor may be turned off, stylet cap 9 unthreaded from housing 11 and inner needle 7 retracted. At the same time, stop cock handle 4 is repositioned such that pressure communication is achieved from the tip of outer needle 6 through stop cock 3 to syringe barrel 1. Syringe plunger 2 is then retracted through syringe barrel 1, negative pressure being transmitted to the tip of outer needle 6 and a sample drawn into needle 6. Subsequently, outer needle 6 is withdrawn from the body of the patient.

It may be noted that pressure monitor 5 need not be a balloon in housing type apparatus as has been described herein, but may take any form of pressure indicator which is sensitive enough to register the small differences in pressure which occur within the chest area. The apparatus may, in fact, be used without such a monitor at all. Experiments have shown, however, that the use of the pressure monitor as described along with the stylet and inner needle design results in improved ability to quickly position the needle tip during the biopsy procedure, thereby resulting in a significant decrease in the occurrence of pneumothorax during lung biopsy. Since a pressure decrease is immediately registered by the pressure monitor as the needle tip enters the lesion or tumor from which a sample is desired, more accurate sampling results.

Although only an exemplary embodiment of invention has been described in detail, those skilled in the art will recognize that many modifications and variations may be made in this embodiment while retaining the novel features and advantages of this invention. Accordingly, all such variations and modifications are intended to be included within the scope of the appended claims.

What is claimed is:

1. A needle assembly for obtaining biopsy tissue from the lung of a patient, said assembly comprising:
   (a) an outer hollow needle;
   (b) an inner hollow needle retractably disposed within said outer needle such that the tip of the inner needle protrudes from the tip of the outer needle when the inner needle is an extended position, and such that the tip of the inner needle is retracted within the tip of the outer needle in a retracted position,
   the outer diameter of the inner needle closely matching the inner diameter of the outer needle;
   (c) a stylet engaged with the proximal end of the inner needle, said stylet being of lesser diameter than said inner needle and extending from the proximal end of the inner needle through the length of the outer needle;
   (d) means for sealing the proximal end of the outer needle, the stylet extending through said sealing means so as to allow retraction and extension of the inner needle within the outer needle while maintaining the seal; and
   (e) means for applying a negative pressure within said outer needle via an opening along the proximal portion thereof.

2. An assembly as in claim 1, wherein said inner needle has a bevelled tip and said outer needle has a flat tip.

3. An assembly as in claim 1, wherein the proximal portion of the stylet extending through said sealing means is engaged with an adjustment cap, such that reciprocal movement of said cap retracts or extends the distal tip of the inner needle with respect to the outer needle.

4. An assembly as in claim 1, wherein the outer needle further comprises an indented portion, said portion limiting the retracting of the inner needle.

5. An assembly as in claim 1 wherein said means for applying a negative pressure within said outer needle comprises a plunger in barrel syringe assembly sealably disposed at right angles to the length of the outer needle.

6. An assembly as in claim 5, further comprising valve means for selectively allowing communication of fluid within the outer needle to said syringe assembly.

7. An assembly as in claim 6, further comprising means for indicating pressure changes within said outer needle, 8. An assembly as in claim 7, wherein said pressure indicating means is engaged with said valve means so that said valve means can be used to selectively allow communication of pressure changes from the outer needle to either the syringe assembly or the pressure change indicating means.

9. A needle assembly for obtaining biopsy tissue from the lung of a patient, said assembly comprising:
  (a) an outer hollow needle;
  (b) an inner hollow needle retractably disposed within said outer needle such that the tip of the inner needle protrudes from the tip of the outer needle when the inner needle is an extended position, and such that the tip of the inner needle is retracted within the tip of the outer needle in a retracted position,
  the outer diameter of the inner needle closely matching the inner diameter of the outer needle;
  (c) a stylet engaged with the proximal end of the inner needle, said stylet being of lesser diameter than said inner needle and extending from the proximal end of the inner needle through the length of the outer needle;
  (d) means for sealing the proximal end of the outer needle, the stylet extending through said sealing means so as to allow retraction and extension of the inner needle within the outer needle while maintaining the seal;
  (e) means for applying a negative pressure within said outer needle via an opening along the proximal portion thereof; and
  (f) means for indicating changes in pressure within said outer needle and mounted on said assembly, said means comprising a balloon which inflates in response to increasing pressure and deflates in response to decreasing pressure.

* * * * *